US007314431B1

(12) United States Patent
Korotiaev

(10) Patent No.: US 7,314,431 B1
(45) Date of Patent: Jan. 1, 2008

(54) VIBRATING DEVICE FOR STRETCHING LEG MUSCLES

(76) Inventor: Alexei Korotiaev, 2627 S. Barrington Ave. #2, Los Angeles, CA (US) 90064

(*) Notice: Subject to any disclaimer, the term of this patent is extended or adjusted under 35 U.S.C. 154(b) by 318 days.

(21) Appl. No.: 11/202,119

(22) Filed: Aug. 12, 2005

(51) Int. Cl.
*A63B 22/00* (2006.01)
*A63B 21/00* (2006.01)
*A61F 5/00* (2006.01)
*A61H 1/00* (2006.01)

(52) U.S. Cl. .......................... 482/51; 482/907; 482/92; 601/26; 606/243

(58) Field of Classification Search ................. 482/51, 482/57, 70, 52, 92, 148, 907; 601/26, 33; 606/243, 245
See application file for complete search history.

(56) References Cited

U.S. PATENT DOCUMENTS 2,152,431 A * 3/1939 Jensen ........................ 606/245
2,179,595 A * 11/1939 McManis .................... 606/245
D219,745 S 1/1971 Windscheffel
3,931,354 A * 1/1976 Sheppard et al. ........... 525/122
3,984,101 A 10/1976 Garza
4,531,730 A * 7/1985 Chenera ..................... 482/142
5,158,568 A 10/1992 Riddle et al.
5,458,618 A * 10/1995 Steinke ....................... 606/242
5,468,216 A * 11/1995 Johnson et al. ............... 601/24
5,500,002 A * 3/1996 Riddle et al. ............... 606/242
5,971,901 A 10/1999 Shaw
6,106,490 A 8/2000 Shaw
6,468,236 B1 10/2002 Sumanac

* cited by examiner

*Primary Examiner*—Stephen R. Crow

(57) ABSTRACT

A device includes a support shaft that has upper and lower sections extending orthogonal to each other and defining an arcuate elbow therebetween. The upper section defines a height of the device and a lower section defines a depth of thereof. A handle bar section is conjoined to the upper section of the support shaft and extends rearwardly therefrom. A seat section is connected to the lower section of the support shaft. The device further includes frame members that have end portions situated medially and laterally beneath the handle bar section. The medial end portions are pivotally conjoined to the support shaft and wheels are connected to the lateral end portions. Each frame member further includes a padded layer centrally registered along a longitudinal length thereof. The frame members have rectangular shapes for providing sufficient surface area on which the user's legs can be supported.

18 Claims, 4 Drawing Sheets

VIBRATING DEVICE FOR STRETCHING LEG MUSCLES

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to vibrating devices and, more particularly, to a vibrating device for stretching leg muscles.

2. Prior Art

It has become common practice for a patient to receive vibrating therapy of some sort, as part of their physical rehabilitation therapy course, after severely over stretching or tearing a muscle. This practice is especially widely used where such muscle injuries have occurred in the lower back region.

Through vibrating the muscles at an ideal frequency, the muscles are caused to involuntarily relax, which results in an advantageous increase in blood flow to those muscles. Such an increased blood flow subsequently causes more oxygen and nutrients to be brought to the injured muscles, thus resulting in a shorter recovery period. With a debilitating injury, this is advantageous, since the person is allowed to return to their normal way of life more rapidly and no longer have to be a burden on those providing care to them.

As has been mentioned before, vibration of certain muscle groups at their ideal frequency causes an involuntary relaxation in those muscles. When the muscles are thus relaxed they can be stretched further, and with less pain, than would be possible without vibrating treatment. Such stretching further increases blood flow to the muscles, the benefits of which has already been discussed above, and also allows a person to attain the full range of motion in that muscle group more rapidly.

One region of muscles that would greatly benefit from such vibrating and stretching treatments are those in the leg regions. As of yet there are no examples of known knowledge in the prior art that provide means for performing such stretching and vibrating treatments on the legs of an injured individual. As can be imagined, an injury to the muscles of a leg severely retards a person's ability to move about and care for themself. Even healthy individuals can benefit from vibrating treatments, since an increased blood flow would allow them to have a more intense workout due to better oxygen circulation to the muscles that are being exercised.

Accordingly, a need remains for a vibrating device for stretching leg muscles in order to overcome the above noted shortcomings. The present invention satisfies such a need by providing a vibrating device for stretching leg muscles that is easy to use, and has the ability to help improve the flexibility and strength of the leg muscles more rapidly. Such a vibrating device allows fitness enthusiasts and those with leg injuries to stretch their muscles while subjecting them to soft vibrations. The vibrations can be adjusted to match the muscles' natural frequency so that the muscles will relax, resulting in increased elasticity and flexibility.

BRIEF SUMMARY OF THE INVENTION

In view of the foregoing background, it is therefore an object of the present invention to provide a vibrating device for stretching leg muscles. These and other objects, features, and advantages of the invention are provided by a power-operable device for assisting a user to effectively stretch leg muscles and improve flexibility.

The device includes an elongated support shaft that has monolithically formed upper and lower sections extending substantially orthogonal to each other. Such upper and lower sections define an elbow that has an arcuate shape wherein the upper section extends parallel to a vertical axis and the lower section extends parallel to a horizontal axis. The upper section terminates at a predetermined distance above the lower section defining a height of the device. Such a lower section extends forwardly from the upper section and terminates at a predetermined distance defining a depth of the device.

A handle bar section is directly conjoined to the upper section of the support shaft and extends rearwardly therefrom at an angle parallel to the lower section. The handle bar section preferably includes first and second handles provided with offset end portions fastened to the support shaft and protruding rearwardly therefrom. Such first and second handles are equidistantly offset from the seat section. A seat section is securely connected to the lower section of the support shaft and protrudes rearwardly from the upper section at an angle parallel to the handle bar section.

The device further includes a plurality of frame members that have opposed end portions situated medially and laterally beneath the handle bar section respectively. Medial ones of such end portions are pivotally and directly conjoined to the support shaft in such a manner that the frame members can effectively be articulated between extended and retracted positions during operating conditions. Each of the frame members include a plurality of wheels operably connected to lateral ones of the end portions for advantageously facilitating a side-to-side motion while the user stands on the frame members and biases the frame members about the lower section of the support shaft.

Each of the frame members is further independently pivotal between horizontal and vertical positions respectively wherein the user's legs become fully extended and positioned parallel to a horizontal ground surface on which the device is supported. Each frame member includes a padded layer centrally registered along a longitudinal length thereof respectively. Such frame members have coextensive rectangular shapes for advantageously providing sufficient surface area on which the user's legs can conveniently be supported.

Each frame member preferably further includes an elongated foot board secured proximate to the lateral end portions respectively. Such foot boards have a substantially planar top surface protruding outwardly from the frame members and at an angle orthogonal thereto for defining a surface area on which the user may conveniently place each foot during operating conditions.

The device may further include a mechanism for vibrating the device during operating conditions such that the frame members and the seat section and the handle bar section vibrate in sync. Such a vibrating mechanism preferably includes a motor situated subjacent to the seat section and operably attached to the support shaft. A power cord is electrically mated to the motor and removably insertable into an electrical outlet.

The vibrating mechanism preferably further includes at least one control dial operably attached to the motor and secured to the upper section of the support shaft. Such at least one control dial is medially situated between the first and second handles such that the user can readily adjust an operating mode of the vibrating mechanism while remaining positioned on the frame members during operating conditions.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

Figure 1:
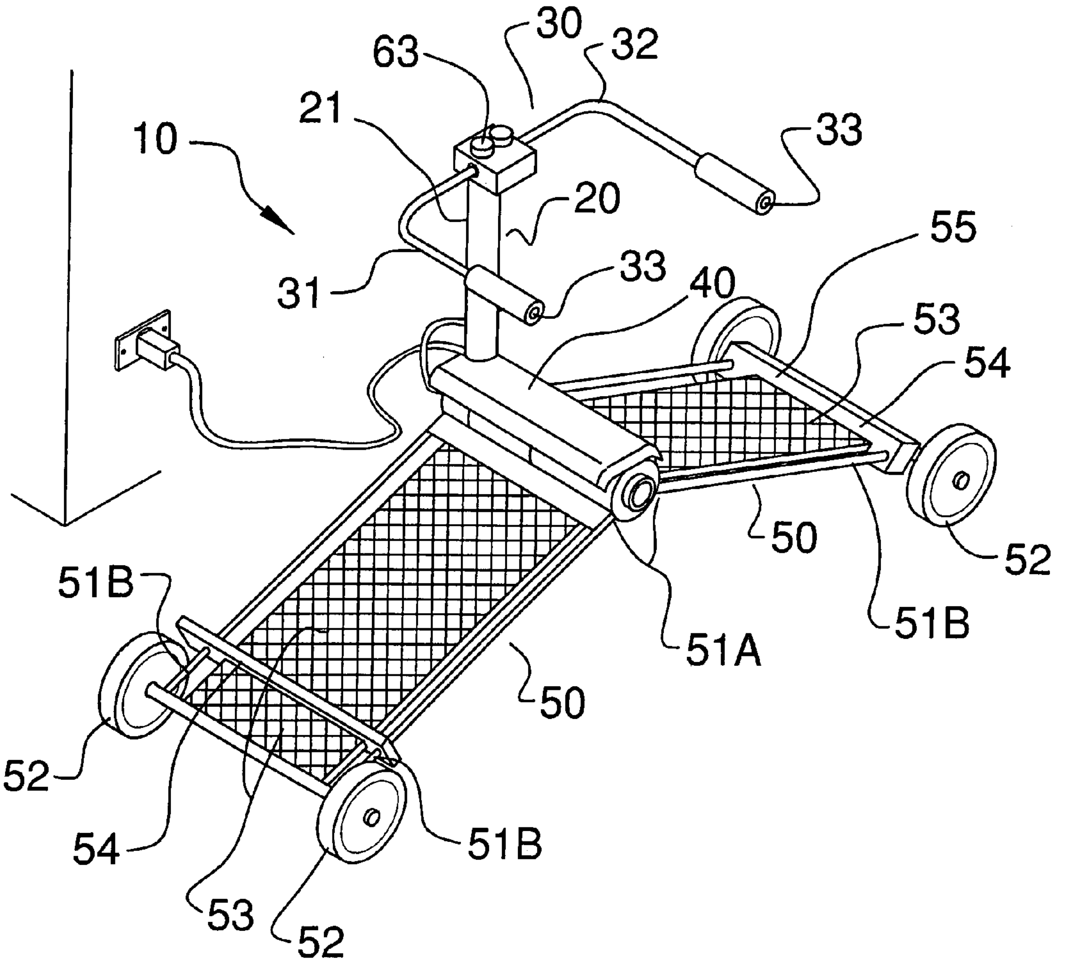
FIG. 1 is a perspective view showing a vibrating device for stretching leg muscles, in accordance with the present invention.

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The device of this invention is referred to generally in FIGS. 1-4 by the reference numeral 10 and is intended to provide a vibrating device for stretching leg muscles. It should be understood that the device 10 may be used to stretch leg muscle at many different types of physical readiness and should not be limited in use to only injured leg muscles. Existing exercise devices do not work to relax muscles. It is commonly known that only relaxed muscles can be stretched without being injured.

Figure 2:
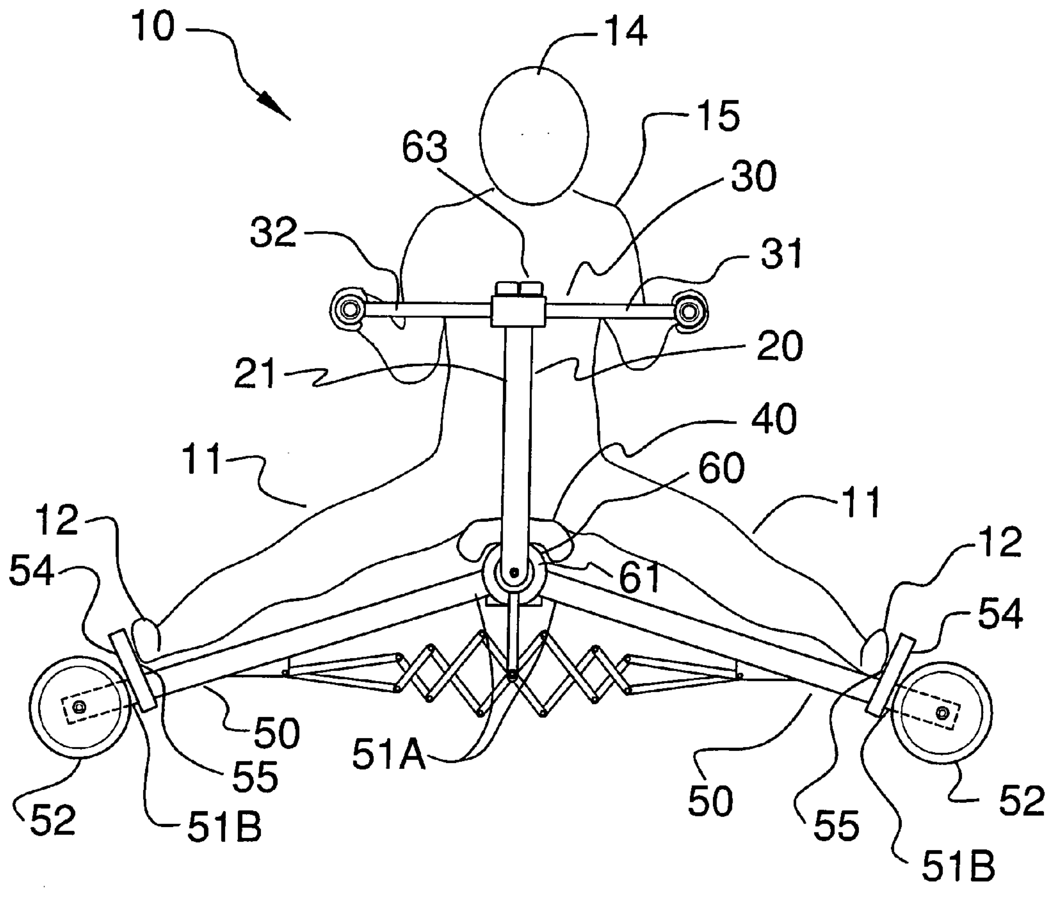
FIG. 2 is a front-elevational view of the device shown in FIG. 1.
Figure 3:
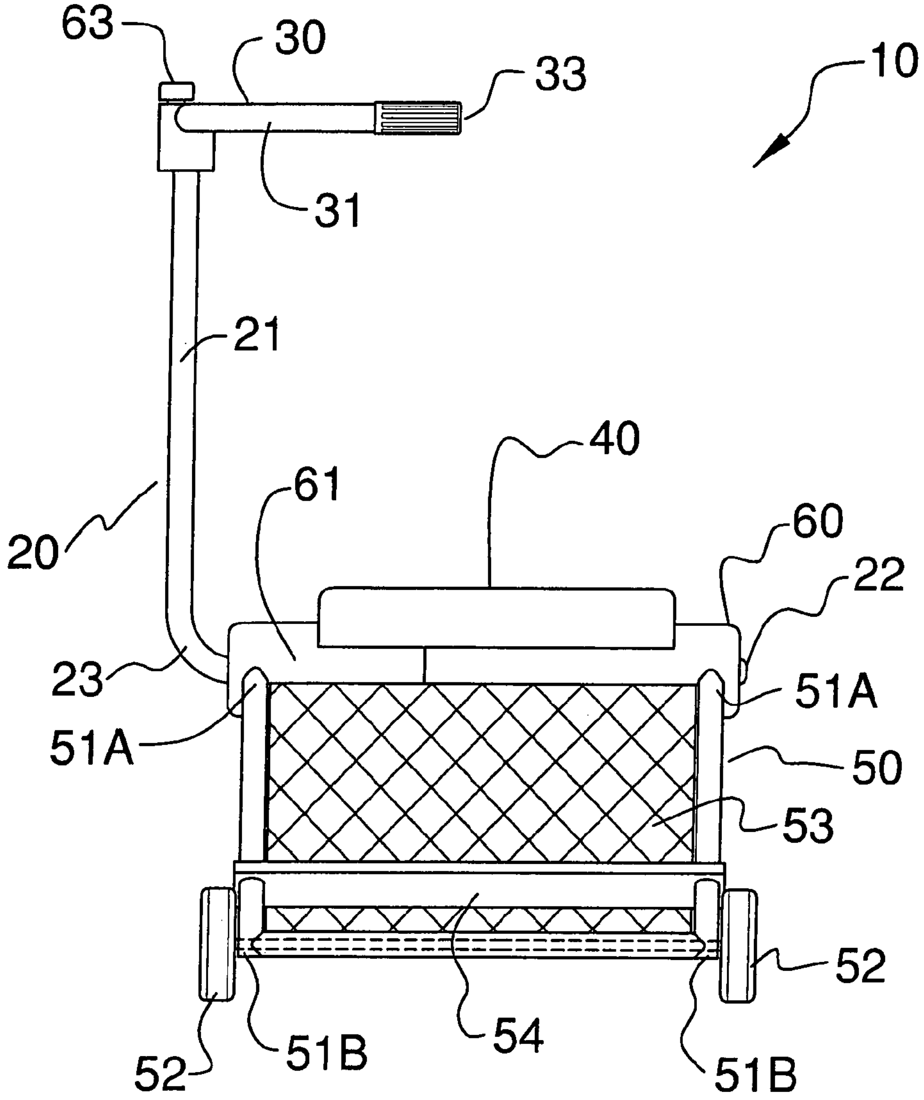
FIG. 3 is a side-elevational view of the device shown in FIG. 1.

Referring initially to FIGS. 1 and 2, the device 10 includes an elongated support shaft 20 that has monolithically formed upper 21 and lower 22 sections extending substantially orthogonal to each other. Such upper 21 and lower 22 sections define an elbow 23 that has an arcuate shape wherein the upper section 21 extends parallel to a vertical axis and the lower section 22 extends parallel to a horizontal axis. The upper section 21 terminates at a predetermined distance above the lower section 22 defining a height of the device 10. Such a lower section 22 extends forwardly from the upper section 21 and terminates at a predetermined distance defining a depth of the device 10.

Referring to FIGS. 1 through 4, a handle bar section 30 is directly conjoined, with no intervening elements, to the upper section 21 of the support shaft 20 and extends rearwardly therefrom at an angle parallel to the lower section 22, such that same may be easily grasped by a user. The handle bar section 30 includes first 31 and second 32 handles provided with offset end portions 33 fastened to the support shaft 20 and protruding rearwardly therefrom. Such first 31 and second 32 handles are equidistantly offset from the seat section 40 (described herein below) which is a vital feature of the device 10 for assisting the user to remain at a balanced position during operating conditions.

Still referring to FIGS. 1 through 4, a seat section 40 is securely connected to the lower section 22 of the support shaft 20 and protrudes rearwardly from the upper section 21 at an angle parallel to the handle bar section 30. The seat section 40 provides a convenient surface for the user 14 to support their upper body 15 upon such that they can use the device 10 for longer periods of time, which subsequently culminates in better results for the user 14.

Again referring to FIGS. 1 through 4, the device 10 further includes a plurality of frame members 50 that have opposed end portions 51 situated medially and laterally beneath the handle bar section 30 respectively. Medial ones 51A of such end portions 51 are pivotally and directly conjoined, with no intervening elements, to the support shaft 20 in such a manner that the frame members 50 can effectively be articulated between extended and retracted positions during operating conditions. Extending and retracting the frame members 50 is essential and advantageous for allowing a user 14 to increase or decrease the amount of stretch experienced by their legs 11. Each of the frame members 50 include a plurality of wheels 52 operably connected to lateral ones 51B of the end portions 51 for advantageously facilitating a side-to-side motion while the user stands on the frame members 50 and biases the frame members 50 about the lower section 22 of the support shaft 20. Such rollers 52 are important for allowing the device 10 to be transported between remote locations.

Figure 4:
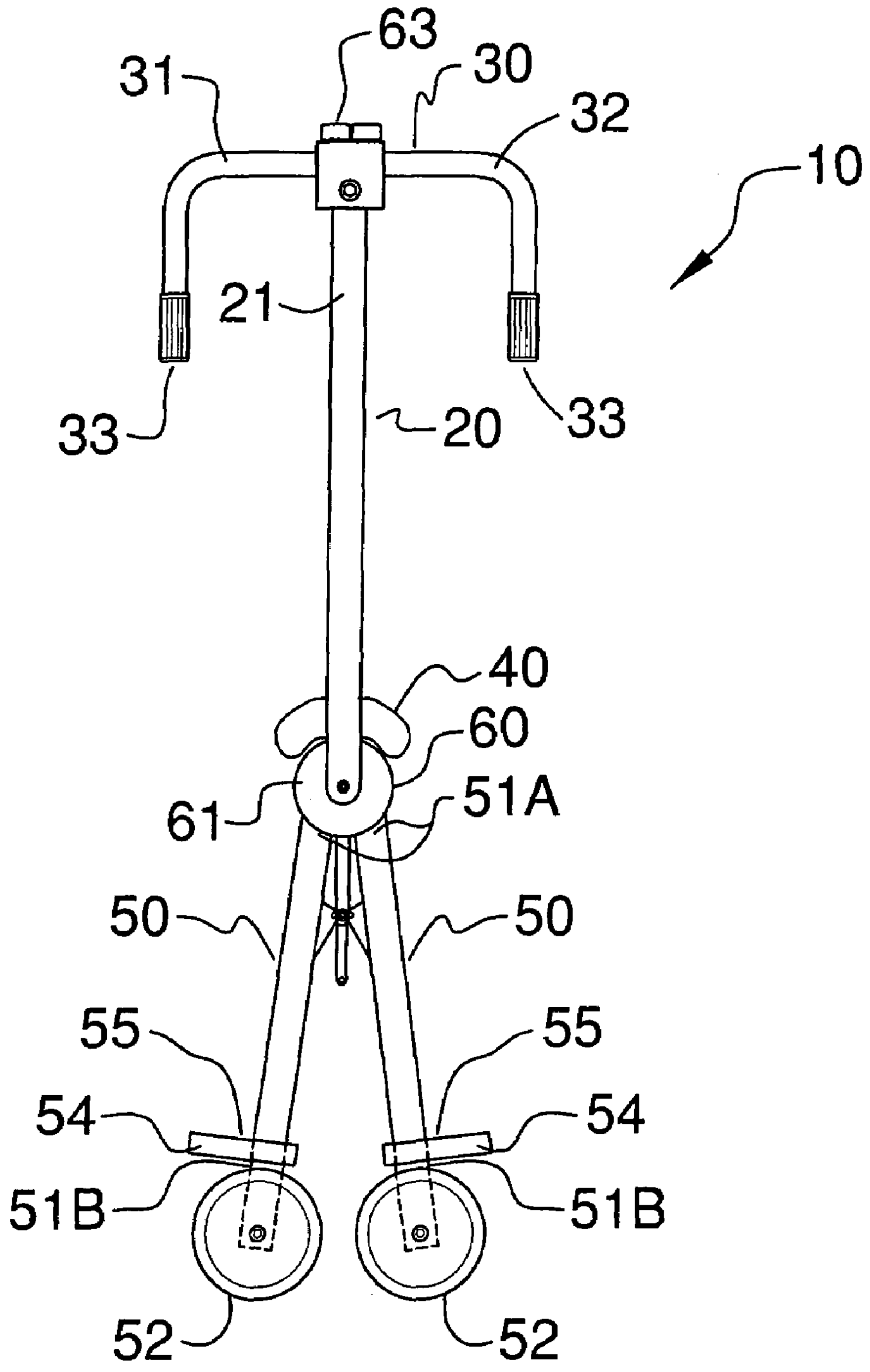
FIG. 4 is a rear-elevational view of the device shown in FIG. 1, showing the frame members at a retracted position prepared for storage conditions.

Referring to FIGS. 2 and 4, each of the frame members 50 is further independently pivotal between horizontal and vertical positions respectively wherein the user's legs 11 become fully extended and positioned parallel to a horizontal ground surface on which the device 10 is supported. Each frame member 50 includes a padded layer 53 centrally registered along a longitudinal length thereof respectively for providing a convenient surface on which the user's legs 11 may rest. Such frame members 50 have coextensive rectangular shapes for advantageously providing sufficient surface area on which the user's legs 11 can conveniently be supported.

Referring to FIGS. 1 through 4, each frame member 50 further includes an elongated foot board 54 secured proximate to the lateral end portions 51B respectively. Such foot boards 54 have a substantially planar top surface 55 protruding outwardly from the frame members 50 and at an angle orthogonal thereto for defining a surface area on which the user may conveniently place each foot 12 during operating conditions. The foot boards 54 may, of course, be vertically adjustable along a longitudinal length of the frame members 50 such that users 14 of differing length may all use the same device 10 by simply adjusting the foot boards 54. Of course, such foot boards 54 may be adjusted manually or with the assistance of an electric motor, similar to one used to lower and raise hospital beds, as well known in the industry.

Still referring to FIGS. 1 through 4, the device 10 further includes a mechanism 60 for vibrating the device 10 during operating conditions such that the frame members 50 and the seat section 40 and the handle bar section 30 vibrate in sync. Such a vibrating mechanism 60 includes a motor 61 situated subjacent to the seat section 40 and operably attached to the support shaft 20. A power cord 62 is electrically mated to the motor 61 and removably insertable into an electrical outlet 13.

Again referring to FIGS. 1 through 4, the vibrating mechanism 60 further includes at least one control dial 63 operably attached to the motor 61 and secured to the upper section 21 of the support shaft 20. Such at least one control dial 63 is medially situated between the first 31 and second 32 handles such that the user can readily adjust an operating mode of the vibrating mechanism 60 while remaining positioned on the frame members 50 during operating conditions.

The use of the vibration mechanism 60 provides muscle relaxation and thus, effective stretching of muscle fibers. Many existing exercise devices do not provide such muscle relaxation while stretching the muscles. These devices apply tension to the leg muscles and further prevent rotation of the hip joints. The control dial 63 is essential to the device 10 for allowing a user 14 to set the rate of vibration equal to the natural frequency required by their leg muscles to relax involuntarily, such that the use of the device 10 is most beneficial. Existing exercise machines include a dial for adjusting the resistance until a user's pain becomes unbearable. The device 10 is designed for use by individuals with limited flexibility or traumas wherein a certain pain threshold can not be exceeded otherwise damage or injury may occur.

The device 10 advantageously provides a professional and scientifically proven method for stretching muscles. Such a device 10 provides an effective, safe, and painless stretching of muscle fibers without injury. The vibration provided by the device 10 provides a "warming up" and relaxing effect on muscle fibers of the legs, and the ligaments of hip joints, increasing their elasticity and thus, the flexibility and stretchability of a user.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A power-operable device for assisting a user to effectively stretch leg muscles and improve flexibility, said device comprising:

an elongated support shaft having monolithically formed upper and lower sections extending substantially orthogonal to each other, said upper and lower sections defining an elbow having an arcuate shape wherein said upper section extends parallel to a vertical axis and said lower section extends parallel to a horizontal axis, said upper section terminating at a predetermined distance above said lower section and defining a height of said device, said lower section extending forwardly from said upper section and terminating at a predetermined distance defining a depth of said device;

a handle bar section directly conjoined to said upper section of said support shaft and extending rearwardly therefrom at an angle parallel to said lower section;

a seat section securely connected to said lower section of said support shaft and protruding rearwardly from said upper section at an angle parallel to said handle bar section; and a plurality of frame members having opposed end portions situated medially and laterally beneath said handle bar section respectively, medial ones of said end portions being pivotally and directly conjoined to said support shaft in such a manner that said frame members can be articulated between extended and retracted positions during operating conditions, each said frame members including a plurality of wheels operably connected to lateral ones of said end portions for facilitating a side-to-side motion while the user stands on said frame members and biases said frame members about said lower section of said support shaft, each said frame member being independently pivotal between horizontal and vertical positions respectively wherein the user's legs become fully extended and positioned parallel to a horizontal ground surface on which said device is supported.

2. The device of claim 1, further comprising: means for vibrating said device during operating conditions such that said frame members and said seat section and said handle bar section vibrate in sync.

3. The device of claim 2, wherein said vibrating means comprises:

a motor situated subjacent said seat section and operably attached to said support shaft; and a power cord electrically mated to said motor and removably insertable into an electrical outlet.

4. The device of claim 1, wherein each said frame member comprises:

an elongated foot board secured proximate to each said lateral end portions respectively, said foot boards having a substantially planar top surface protruding outwardly from said frame members and at an angle orthogonal thereto for defining a surface area on which the user may place each foot during operating conditions.

5. The device of claim 1, wherein said handle bar section comprises: first and second handles provided with offset end portions directly fastened to said support shaft and protruding rearwardly therefrom, said first and second handles being equidistantly offset from said seat section.

6. The device of claim 5, wherein said vibrating means further comprises:

at least one control dial operably attached to said motor and directly secured to said upper section of said support shaft, said at least one control dial being medially situated between said first and second handles such that the user can readily adjust an operating mode of said vibrating means while remaining positioned on said frame members during operating conditions.

7. A power-operable device for assisting a user to effectively stretch leg muscles and improve flexibility, said device comprising:

an elongated support shaft having monolithically formed upper and lower sections extending substantially orthogonal to each other, said upper and lower sections defining an elbow having an arcuate shape wherein said upper section extends parallel to a vertical axis and said lower section extends parallel to a horizontal axis, said upper section terminating at a predetermined distance above said lower section and defining a height of said device, said lower section extending forwardly from said upper section and terminating at a predetermined distance defining a depth of said device;

a handle bar section directly conjoined to said upper section of said support shaft and extending rearwardly therefrom at an angle parallel to said lower section;

a seat section securely connected to said lower section of said support shaft and protruding rearwardly from said upper section at an angle parallel to said handle bar section; and a plurality of frame members having opposed end portions situated medially and laterally beneath said handle bar section respectively, medial ones of said end portions being pivotally and directly conjoined to said support shaft in such a manner that said frame members can be articulated between extended and retracted positions during operating conditions, each said frame members including a plurality of wheels operably connected to lateral ones of said end portions for facilitating a side-to-side motion while the user stands on said frame members and biases said frame members about said lower section of said support shaft, each said frame members being independently pivotal between horizontal and vertical positions respectively wherein the user's legs become fully extended and positioned parallel to a horizontal ground surface on which said device is supported, each said frame members includes a padded layer centrally registered along a longitudinal length thereof respectively.

8. The device of claim 7, further comprising: means for vibrating said device during operating conditions such that said frame members and said seat section and said handle bar section vibrate in sync.

9. The device of claim 8, wherein said vibrating means comprises:

a motor situated subjacent said seat section and operably attached to said support shaft; and a power cord electrically mated to said motor and removably insertable into an electrical outlet.

10. The device of claim 7, wherein each said frame member comprises:

an elongated foot board secured proximate to each said lateral end portions respectively, said foot boards having a substantially planar top surface protruding outwardly from said frame members and at an angle orthogonal thereto for defining a surface area on which the user may place each foot during operating conditions.

11. The device of claim 7, wherein said handle bar section comprises: first and second handles provided with offset end portions fastened to said support shaft and protruding rearwardly therefrom, said first and second handles being equidistantly offset from said seat section.

12. The device of claim 11, wherein said vibrating means further comprises: at least one control dial operably attached to said motor and secured to said upper section of said support shaft, said at least one control dial being medially situated between said first and second handles such that the user can readily adjust an operating mode of said vibrating means while remaining positioned on said frame members during operating conditions.

13. A power-operable device for assisting a user to effectively stretch leg muscles and improve flexibility, said device comprising:

an elongated support shaft having monolithically formed upper and lower sections extending substantially orthogonal to each other, said upper and lower sections defining an elbow having an arcuate shape wherein said upper section extends parallel to a vertical axis and said lower section extends parallel to a horizontal axis, said upper section terminating at a predetermined distance above said lower section and defining a height of said device, said lower section extending forwardly from said upper section and terminating at a predetermined distance defining a depth of said device;

a handle bar section directly conjoined to said upper section of said support shaft and extending rearwardly therefrom at an angle parallel to said lower section;

a seat section securely connected to said lower section of said support shaft and protruding rearwardly from said upper section at an angle parallel to said handle bar section; and a plurality of frame members having opposed end portions situated medially and laterally beneath said handle bar section respectively, medial ones of said end portions being pivotally and directly conjoined to said support shaft in such a manner that said frame members can be articulated between extended and retracted positions during operating conditions, each said frame members including a plurality of wheels operably connected to lateral ones of said end portions for facilitating a side-to-side motion while the user stands on said frame members and biases said frame members about said lower section of said support shaft, each said frame members being independently pivotal between horizontal and vertical positions respectively wherein the user's legs become fully extended and positioned parallel to a horizontal ground surface on which said device is supported, each said frame members includes a padded layer centrally registered along a longitudinal length thereof respectively, said frame members have coextensive rectangular shapes for providing sufficient surface area on which the user's legs can be supported.

14. The device of claim 13, further comprising: means for vibrating said device during operating conditions such that said frame members and said seat section and said handle bar section vibrate in sync.

15. The device of claim 14, wherein said vibrating means comprises:

a motor situated subjacent said seat section and operably attached to said support shaft; and a power cord electrically mated to said motor and removably insertable into an electrical outlet.

16. The device of claim 13, wherein each said frame member comprises:

an elongated foot board secured proximate to each said lateral end portions respectively, said foot boards having a substantially planar top surface protruding outwardly from said frame members and at an angle orthogonal thereto for defining a surface area on which the user may place each foot during operating conditions.

17. The device of claim 13, wherein said handle bar section comprises:

first and second handles provided with offset end portions fastened to said support shaft and protruding rearwardly therefrom, said first and second handles being equidistantly offset from said seat section.

18. The device of claim 17, wherein said vibrating means further comprises: at least one control dial operably attached to said motor and secured to said upper section of said support shaft, said at least one control dial being medially situated between said first and second handles such that the user can readily adjust an operating mode of said vibrating means while remaining positioned on said frame members during operating conditions.

* * * * *